(12) United States Patent
Allen et al.

(10) Patent No.: US 11,404,147 B2
(45) Date of Patent: Aug. 2, 2022

(54) TREATMENT RECOMMENDATIONS BASED ON DRUG-TO-DRUG INTERACTIONS

(71) Applicant: International Business Machines Corporation, Armonk, NY (US)

(72) Inventors: Corville O. Allen, Morrisville, NC (US); Timothy A. Bishop, Minneapolis, MN (US); Michael T. Payne, Rochester, MN (US); Sue S. Schmidt, Rochester, MN (US); Leah R. Smutzer, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 1239 days.

(21) Appl. No.: 15/587,949

(22) Filed: May 5, 2017

(65) Prior Publication Data
US 2018/0322249 A1    Nov. 8, 2018

(51) Int. Cl.
*G16H 10/60* (2018.01)
*G16H 50/20* (2018.01)
*G16H 20/10* (2018.01)

(52) U.S. Cl.
CPC .............. *G16H 10/60* (2018.01); *G16H 20/10* (2018.01); *G16H 50/20* (2018.01)

(58) Field of Classification Search
CPC ........ G06Q 30/00; G06Q 50/22; G06Q 30/06; G06Q 10/1097; G06Q 30/02; G06Q 50/01; G06Q 50/00; G06Q 40/00; G06H 10/60; G06F 19/3418; G06F 17/00; G06F 19/00; G05B 15/02; H04R 3/00; H04L 12/2827; G16H 50/30
See application file for complete search history.

(56) References Cited

U.S. PATENT DOCUMENTS 6,081,786 A * 6/2000 Barry et al.
8,032,394 B1   10/2011 Ghouri
8,884,752 B2   11/2014 Tai et al.
(Continued)

OTHER PUBLICATIONS

List of IBM Patents or Patent Applications Treated as Related, Oct. 31, 2018, 2 pages.
(Continued)

*Primary Examiner* — Jason S Tiedeman
*Assistant Examiner* — William T. Monticello
(74) *Attorney, Agent, or Firm* — Stephen J. Walder, Jr.; Gavon Pontikos

(57) ABSTRACT

Cognitive medical treatment recommendation mechanisms are provided. The mechanisms ingest a corpus of medical treatment content that comprises drug-to-drug interaction information. The mechanisms generate a set of drug interaction insight data structures and an initial set of candidate treatments for a medical condition of a patient based on an analysis of an electronic medical record associated with the patient. The mechanisms rank candidate treatments in the initial set of candidate treatments based on the set of drug interaction insight data structures to generate a final set of candidate treatments, where the ranking reduces rankings of candidate treatments in which drug interactions are identified in the set of drug interaction insight data structures. The mechanisms output a treatment recommendation based on the final set of candidate treatments.

20 Claims, 6 Drawing Sheets

(56) References Cited

U.S. PATENT DOCUMENTS

| | | | |
|---|---|---|---|
| 9,465,969 | B2 | 10/2016 | Seo et al. |
| 10,354,202 | B2 | 7/2019 | Tatonetti et al. |
| 2001/0001144 | A1 | 5/2001 | Kapp |
| 2001/0032099 | A1 | 10/2001 | Joao |
| 2003/0050802 | A1 | 3/2003 | Jay et al. |
| 2003/0099158 | A1 | 5/2003 | De la Huerga |
| 2004/0010511 | A1 | 1/2004 | Gogolak |
| 2005/0203771 | A1 | 9/2005 | Achan |
| 2006/0015518 | A1 | 1/2006 | Eletreby et al. |
| 2006/0036619 | A1 | 2/2006 | Fuerst et al. |
| 2006/0261145 | A1 | 11/2006 | Robertson et al. |
| 2008/0171916 | A1* | 7/2008 | Feder et al. |
| 2008/0185425 | A1 | 8/2008 | Roberts et al. |
| 2009/0125335 | A1 | 5/2009 | Manetta et al. |
| 2010/0049756 | A1 | 2/2010 | Chemitiganti et al. |
| 2010/0235378 | A1 | 9/2010 | Armstrong et al. |
| 2010/0274586 | A1 | 10/2010 | Choi et al. |
| 2011/0184755 | A1 | 7/2011 | Yamaga et al. |
| 2011/0246221 | A1 | 10/2011 | Camp et al. |
| 2012/0065992 | A1 | 3/2012 | Davis |
| 2012/0078840 | A1 | 3/2012 | Avinash et al. |
| 2012/0116809 | A1 | 5/2012 | Schaap |
| 2012/0179481 | A1 | 7/2012 | Patel et al. |
| 2012/0209625 | A1* | 8/2012 | Armstrong et al. |
| 2012/0253139 | A1 | 10/2012 | Maman et al. |
| 2013/0085765 | A1* | 4/2013 | Tuchinda et al. |
| 2013/0104077 | A1 | 4/2013 | Felt |
| 2013/0132308 | A1 | 5/2013 | Boss et al. |
| 2013/0144584 | A1 | 6/2013 | Chen et al. |
| 2013/0150748 | A1 | 6/2013 | Jensen |
| 2013/0179178 | A1* | 7/2013 | Vemireddy et al. |
| 2013/0179187 | A1* | 7/2013 | Jackson et al. |
| 2014/0006055 | A1 | 1/2014 | Seraly et al. |
| 2014/0058742 | A1 | 2/2014 | Chari et al. |
| 2014/0088982 | A1 | 3/2014 | Argue et al. |
| 2014/0236630 | A1* | 8/2014 | Murata |
| 2014/0249831 | A1 | 9/2014 | Gallopyn et al. |
| 2014/0275853 | A1 | 9/2014 | Needham et al. |
| 2014/0310025 | A1 | 10/2014 | Sayada et al. |
| 2014/0330577 | A1 | 11/2014 | Herman et al. |
| 2015/0019241 | A1 | 1/2015 | Bennett et al. |
| 2015/0106112 | A1 | 4/2015 | Jackson et al. |
| 2015/0120313 | A1 | 4/2015 | Cho et al. |
| 2015/0142701 | A1 | 5/2015 | Ashparie et al. |
| 2015/0169825 | A1 | 6/2015 | Eletreby et al. |
| 2015/0228180 | A1 | 8/2015 | Tai et al. |
| 2015/0269342 | A1 | 9/2015 | Swagger |
| 2015/0379219 | A1 | 12/2015 | Jackson et al. |
| 2016/0048655 | A1 | 2/2016 | Maitra et al. |
| 2016/0071432 | A1 | 3/2016 | Kurowski et al. |
| 2016/0078182 | A1* | 3/2016 | Allen et al. |
| 2016/0103960 | A1 | 4/2016 | Hume et al. |
| 2016/0306948 | A1 | 10/2016 | Chen et al. |
| 2016/0357929 | A1* | 12/2016 | Ghouri et al. |
| 2017/0027505 | A1 | 2/2017 | Dellimore et al. |
| 2017/0061079 | A1* | 3/2017 | LaValley |
| 2017/0235912 | A1* | 8/2017 | Moturu et al. |
| 2017/0253928 | A1* | 9/2017 | Zhu et al. |
| 2017/0286622 | A1* | 10/2017 | Cox et al. |
| 2017/0308655 | A1 | 10/2017 | Carlson et al. |
| 2017/0316175 | A1 | 11/2017 | Hu |
| 2017/0344550 | A1* | 11/2017 | Fischer et al. |
| 2018/0001184 | A1 | 1/2018 | Tran et al. |
| 2018/0102190 | A1* | 4/2018 | Hogue et al. |
| 2018/0211726 | A1* | 6/2018 | Courtemanche et al. |
| 2018/0342323 | A1* | 11/2018 | Shankar et al. |
| 2019/0057182 | A1* | 2/2019 | Klement et al. |

OTHER PUBLICATIONS

Athenahealth—http://landing.athenahealth.com/; accessed from the Internet May 25, 2016, 14 pages.

List of IBM Patents or Patent Applications Treated as Related, Feb. 12, 2018, 2 pages.

U.S. Appl. No. 15/262,311, filed Sep. 12, 2016.

"Drug Interactions Checker", Drugs.com, http://www.drugs.com/drug_interactions.html, accessed from the Internet on May 25, 2016, 1 page.

"Drugs and Drug Interaction", UpToDate, http://www.uptodate.com/home/drugs-drug-interaction, accessed on the Internet on Dec. 14, 2016, 2 pages.

"Electronic Health Records (EHR)", TELUS Health, https://www.telushealth.co/health-solutions/electronic-health-records/products/telus-drug-information-system-dis/, accessed on May 25, 2016, 4 pages.

Gold Standard Drug Database, Elsevier, https://www.elsevier.com/solutions/drug-database, Accessed from the Internet on Feb. 2, 2018, 7 pages.

"How can electronic health records help me prevent adverse medication events?", HealthIT.gov website, https://www.healthit.gov/providers-professionals/faqs/how-can-electronic-health-records-help-me-prevent-adverse-medication-ev, accessed on May 25, 2016, 2 pages.

"Multi-Drug Interaction Checker", Medscape, http://reference.medscape.com/drug-interactionchecker, access from the Internet on May 25, 2016, 1 page.

"The Era of Cognitive Systems: An inside look at IBM Watson and how it works", IBM Corporation, IBM Software Group, Whitepaper, IBM Watson Solutions, Sep. 2012, 19 pages.

WebMD Interaction Checker, WebMD, http://www.webmd.com/interaction-checker/, accessed from the Internet on May 25, 2016, 4 pages.

Boyce, Richard et al., "Using Natural Language Processing to Identify Pharmacokinetic Drug-Drug Interactions Described in Drug Package Inserts", Proceedings of the 2012 Workshop on Biomedical Natural Language Processing (BioNLP 2012, Jun. 8, 2012, pp. 206-213.

Del Fiol, Guilherme et al., "Design, Implementation and Evaluation of a Clinical Decision Support System to Prevent Adverse Drug Events", Studies in Health Technology and Informatics, https://www.ncbi.nlm.nih.gov/pubmed/11187651, 2000, pp. 740-744 (Abstract submitted).

Deleger, Louise et al., "Building Gold Standard Corpora for Medical Natural Language Processing Tasks", AMIA Annual Symposium Proceedings 2012, Nov. 3, 2012, pp. 144-153.

Demner-Fushman, Dina et al., "What can Natural Language Processing do for Clinical Decision Support?", J Biomed Inform., Author Manuscript, 42(5), Oct. 2009, pp. 760-772.

Fung, Kin Wah et al., "Extracting drug indication information from structured product labels using natural language processing", Journal of the American Medical Informatics Association, May 1, 2013, pp. 482-488.

High, Rob, "The Era of Cognitive Systems: An Inside Look at IBM Watson and How it Works", IBM Corporation, Redbooks, Dec. 12, 2012, 16 pages.

Koutkias, Vassilis et al., "Constructing Clinical Decision Support Systems for Adverse Drug Even Prevention: A Knowledge-based Approach", AMIA 2010 Symposium Proceedings, Nov. 13, 2010, pp. 402-406.

Kuperman, Gilad J. et al., "Medication-related Clinical Decision Support in Computerized Provider Order Entry Systems: A Review", Journal of the American Medical Informatics Association, vol. 14, No. 1, Jan./Feb. 2007, pp. 29-40.

Rindflesch, Thomas C. et al., "EDGAR: Extraction of Drugs, Genes and Relations from the Biomedical Literature", National Institute of Health Public Access, Author Manuscript, PAC Symp Biocomput., 2000, pp. 517-528, 12 pages.

Shimada, Kazuyuki et al., "Drug-Recommendation System for Patients with Infectious Diseases", AMIA 2005 Symposium Proceedings, Oct. 22-Oct. 26, 2005, pp. 1112.

Tilson, Hugh et al., "Recommendations for selecting drug-drug interactions for clinical decision support", Am J Health-Syst Pharm, vol. 73, No. 8, Apr. 15, 2016, pp. 576-585.

Wiesner, Martin et al., "Health Recommender Systems: Concepts, Requirements, Technical Basics and Challenges", International Journal of Environmental Research and Public Health, Mar. 3, 2014, 28 pages.

(56) References Cited

OTHER PUBLICATIONS

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

Ayvaz, Serkan et al., "Toward a Complete Dataset of Drug-Drug Interaction Information from Publicly Available Sources", Ayvaz et al., Toward a Complete Dataset of Drug-Drug Interaction Information from Publicly Available Sources, in 55 J. Biomedical Informatics 206-17, Jun. 2015, 28 pages.

Percha, Bethany, "Discovering New Drug-Drug Interactions by Text-Mining the Biomedical Literature", Percha, Discovering New Drug-Drug Interactions by Text-Mining the Biomedical Literature, in 602.43 Drugs 344, Department of Biomedical Informatics, Stanford University, Mar. 2011, 7 pages.

Cao, D-S et al., "Integrating Multiple Evidence Sources to Predict Adverse Drug ReactionsBased on a Systems Pharmacology Model", CPT Pharmacometrics Syst. Pharmacol 4, Sep. 2015, pp. 498-506.

* cited by examiner

500

| STATEMENT PATTERNS | DELTA EXCLUSION SCORE | STATEMENT TYPE | CONDITION(S) |
|---|---|---|---|
| | | | |
| DOSAGE INCREASE MAY BE REQUIRED | 0 | DOSAGE | |
| INCREASE DOSAGE | 0 | DOSAGE | |
| ... | ... | ... | ... |
| DO NOT DRIVE OR OPERATE MACHINERY | 0 | MONITOR | |
| ... | ... | ... | ... |
| USE COMBINATION WITH CAUTION | 0.06 | CAUTION | |
| ... | ... | ... | ... |
| ADMINISTER SEPARATELY | 0.05 | DO NOT MIX | |
| ... | ... | ... | ... |
| MONITOR SERUM ELECTROLYTES | 0.03 | MONITOR | SERUM ELECTROLYTES |
| MONITOR CARDIAC FUNCTION | 0.08 | MONITOR SEVERE CONDITION | CARDIAC FUNCTION |
| MONITOR THYROID FUNCTION | 0.07 | MONITOR SEVERE CONDITION | THYROID FUNCTION |
| MONITOR BLOOD GLUCOSE CONCENTRATION | 0.02 | CAUTION | GLUCOSE |
| MONITOR BLOOD PRESSURE | 0.02 | CAUTION | HIGH BLOOD PRESSURE |
| ... | ... | ... | ... |

FIG. 5

TREATMENT RECOMMENDATIONS BASED ON DRUG-TO-DRUG INTERACTIONS

BACKGROUND

The present application relates generally to an improved data processing apparatus and method and more specifically to mechanisms for providing treatment recommendations for patients that take into account drug-to-drug interactions.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a cognitive medical treatment recommendation system. The method comprises ingesting, by the cognitive medical treatment recommendation system, a corpus of medical treatment content, wherein the medical treatment content comprises drug-to-drug interaction information. The method also comprises generating, by the cognitive medical treatment recommendation system, a set of drug interaction insight data structures based on the ingested corpus of medical treatment content. Moreover, the method comprises generating, by the cognitive medical treatment recommendation system, an initial set of candidate treatments for a medical condition of a patient based on an analysis of one or more electronic medical records (EMRs) associated with the patient. In addition, the method comprises ranking, by the cognitive medical treatment recommendation system, candidate treatments in the initial set of candidate treatments based on the set of drug interaction insight data structures to generate a final set of candidate treatments, wherein the ranking reduces rankings of candidate treatments in which drug interactions are identified in the set of drug interaction insight data structures. Furthermore, the method comprises outputting, by the cognitive medical treatment recommendation system, a treatment recommendation based on the final set of candidate treatments.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 5 illustrates an example of a drug-to-drug (D2D) interaction resource data structure in accordance with one illustrative embodiment.

DETAILED DESCRIPTION

Figure 1:
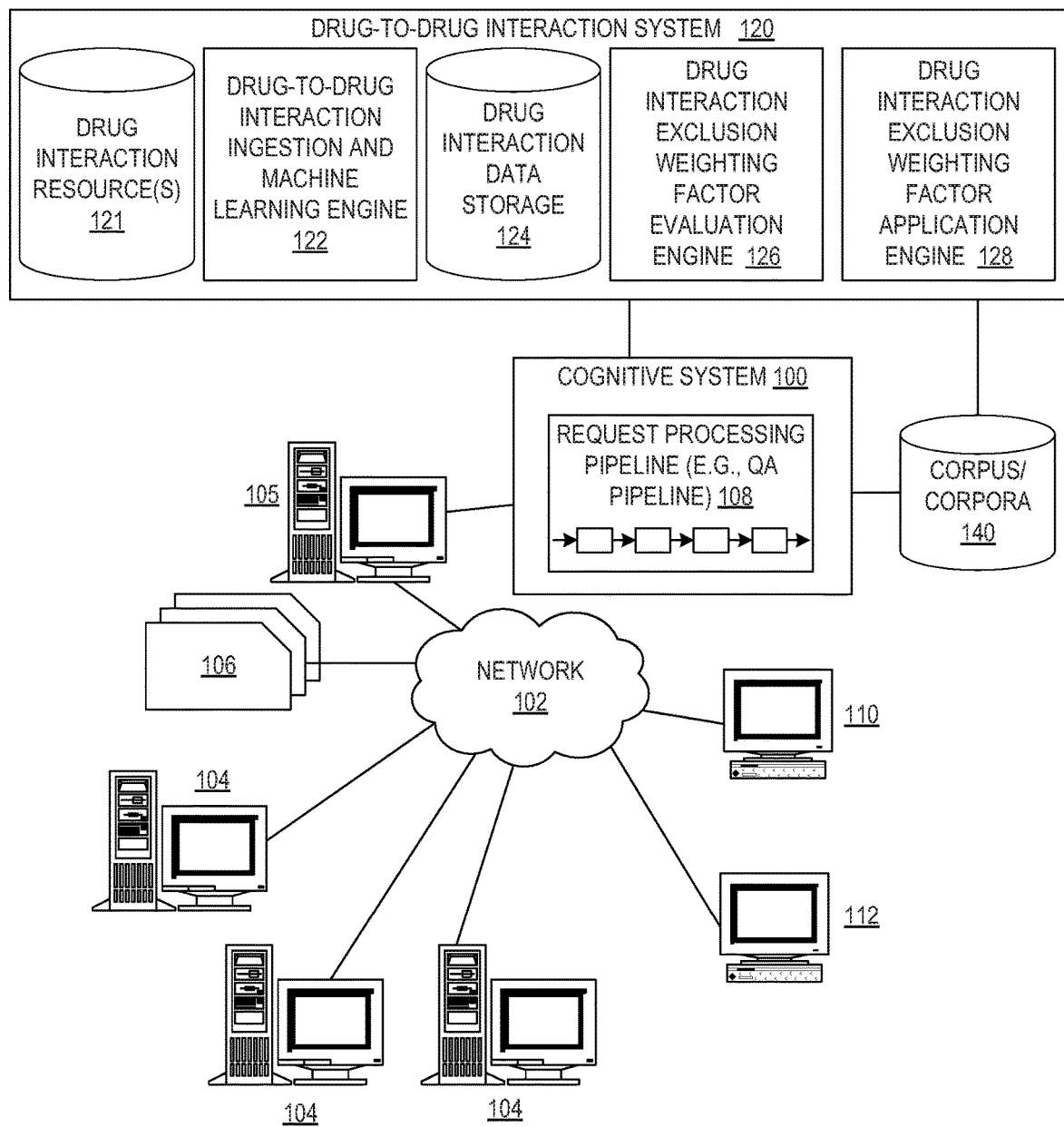
FIG. 1 depicts a schematic diagram of one illustrative embodiment of a cognitive healthcare system in a computer network.

The strengths of current cognitive systems, such as current medical diagnosis, patient health management, patient treatment recommendation systems, law enforcement investigation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients. In particular, one drawback of current systems is the ability to learn and take into consideration drug-to-drug interactions when generating treatment recommendations for patients.

That is, one of the key ways to treat various medical conditions, e.g., diseases, is to place the patient on a treatment regimen that requires the administering of multiple medications, drugs, supplements, or the like (referred to collectively herein as "drugs"). For example, in treating Diabetes Type II, a first line treatment is typically a single drug while a second line treatment may comprise multiple drugs, e.g., metformin and another drug that may depend on the particular patient condition. Even though precautions are taken to avoid negative interactions of drugs, medical personnel are not always aware of all of the possible negative interactions. Moreover, there may be interactions based on the patient's particular attributes and comorbidities that make using treatments involving multiple drugs an issue, which may not be readily apparent to the medical personnel. Furthermore, patients often have more than one medical condition, e.g., chronic diseases, and may be on different drugs for the different medical conditions, leading to additional potential for negative interactions of drugs.

Information regarding drug-to-drug interactions are often found in natural language documentation such as clinical statements, guidelines, and in some patient statements. Drug-to-drug interaction information is provided by drug manufacturers, health organizations, governmental organizations, and other sources in various forms. One example of a source of drug information that includes drug-to-drug interaction information, is the Gold Standard Drug Database, available from Elsevier.

The illustrative embodiments provide mechanisms to parse and analyze, using natural language processing (NLP) mechanisms of a cognitive medical treatment recommendation system, drug-to-drug interaction information in drug label information, clinical statements, patient statements, and the like, so as to categorize the type of interaction based on the interaction statement type (e.g., monitor, dosage adjustment, warning, sever, do not combine, etc.), medical concepts involved (e.g., organs, vitals, psychological, mental capabilities, etc.), possible conditions that may occur, and the like. Based on results of the parsing and analysis of the drug-to-drug interaction information, exclusion weighting factors are applied to candidate treatments for a patient involving a drug and the one or more other drugs with which the drug may have an interaction. The exclusion weighting factor may then be used when selecting a candidate treatment for recommendation of a treatment to treat the patient. In some embodiments, a ranked listing of candidate treatments is generated with the ranking being based on the exclusion weighting factors. A resulting recommendation output may be output to a medical practitioner which may include an explanation as to the reason for the applied exclusion weighting factor, among other information provided regarding the candidate treatment(s) included in the recommendation output.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for learning and applying drug-to-drug interaction information to the evaluation of candidate treatments for patients based on the drugs that are being taken by the patient, the drugs involved in a potential multi-drug treatment regimen, and other patient characteristics, medical conditions, and the like. The illustrative embodiments, as mentioned above, perform natural language processing on natural language descriptions of drug-to-drug interaction information, such as may be provided in various types of medical documentation including, but not limited to, drug label information in electronic drug label documentation, clinical statements in various medical resource publications (e.g., drug desk reference documents) and medical industry publications (e.g., manufacturer produced documentation, governmental organization documentation, medical journals, published medical papers, medical research documents, etc.) present as electronic documentation, and patient information and statements (e.g., patient electronic medical record (EMR) notations, anecdotal statements on patient support websites, etc.). These various natural language document sources may collectively be provided or organized into a corpus or a plurality of corpora of medical documentation which may be ingested and processed by natural language processing (NLP) mechanisms of the illustrative embodiments.

Based on the drug-to-drug interaction information obtained through natural language processing of the various drug interaction source documentation of the corpus or corpora, candidate treatments for a patient based on the patient's medical condition(s) may be evaluated with appropriate exclusionary weightings applied due to drug-to-drug interactions that may exist with other drugs the patient may be taking, such as for other medical conditions, and/or other drugs in a candidate treatment regimen. Such evaluation may take into account many factors of the drug-to-drug interaction including the severity of the interactions, the types of potential resulting medical conditions that may occur from the interaction, particular medical concepts affected by the drug interaction, and the like. Thereafter, once the drug-to-drug interaction considerations are evaluated for the various candidate treatments, one or more candidate treatments may be selected for use in treating the patient and an appropriate output may be generated.

The illustrative embodiments may be utilized in many different types of data processing environments. In order to provide a context for the description of the specific elements and functionality of the illustrative embodiments, FIGS. 1-4 are provided hereafter as example environments in which aspects of the illustrative embodiments may be implemented. It should be appreciated that FIGS. 1-4 are only examples and are not intended to assert or imply any limitation with regard to the environments in which aspects or embodiments of the present invention may be implemented. Many modifications to the depicted environments may be made without departing from the spirit and scope of the present invention.

FIGS. 1-4 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for generating treatment recommendations for patients based on a cognitive evaluation of their medical condition(s), patient attributes, available candidate treatments as indicated in one or more corpora of medical documentation, and the like. In particular, with specific importance to the present application, drug-to-drug interaction information is learned and applied during evaluation of candidate treatments for the patient so as to select and present treatment recommendations that take into consideration the drug-to-drug interactions of the various treatments as well as with other drugs the patient may be taking for other medical conditions.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What treatment applies to patient P?", the cognitive system may instead receive a request of "generate a treatment for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to providing treatment recommendations for patients that take into consideration drug-to-drug interactions when evaluating the efficacy of the treatment for a particular patient and the particular patient's attributes, medical condition(s), other drugs being taken for treatment of the same or other medical conditions, and the like. In taking into account the drug-to-drug interactions, the mechanisms of the illustrative embodiments determine an exclusion factor for a candidate treatment based on learned drug-to-drug interactions and the patient's own personal medical conditions, attributes, and treatments, such as may be determined from patient electronic medical records (EMRs). The exclusion factor may be applied to candidate treatments, which may be candidate "answers" generated by the cognitive system for the question of how to treat the patient for a specific medical condition, so as to modify the ranking or confidence values associated with such candidate treatments as viable treatments for the particular patient. The resulting ranked listing of candidate treatments may then be used to select one or more treatment recommendations to be output to a medical practitioner to assist the medical practitioner is treating the patient.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-4 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, drug-to-drug interaction information in natural language documents, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In some illustrative embodiments, the cognitive system 100 is a cognitive healthcare system that provides medical treatment recommendations for patients and their medical condition(s) based on a variety of factors which includes, among other factors, drug-to-drug interactions as learned and applied by the mechanisms of one or more of the illustrative embodiments described herein.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a drug-to-drug interaction system 120 that ingests drug-to-drug interaction information from one or more sources of electronic documentation provided in natural language format with or without structured content, such as tables, charts, etc., which may be provided in one or more corpora 140, and learns through a machine learning process, the drug-to-drug interactions for various drugs. The drug-to-drug interaction system 120 further evaluates the specific information for a patient, such as the medical condition(s) of the patient for which a treatment involving a drug of interest is being considered, other medical conditions of the patient and associated drugs and other treatments being used to treat these other medical conditions, patient health and demographic attributes, etc., and determines one or more exclusion weighting factors associated with the drug based on corresponding drug-to-drug interactions and the candidate treatments involving the drug which are being considered to treat the patient's medical condition(s). This exclusion weighting factor is then applied to the confidence scores or rankings of the candidate treatments involving the drug via the cognitive system 100 to generate one or more treatment recommendations for the patient.

As shown in FIG. 1, the drug-to-drug interaction system 120 comprises drug interaction resources 121, a drug-to-drug interaction ingestion and machine learning engine 122, a drug interaction data structure storage 124, a drug interaction exclusion weighting factor evaluation engine 126, and a drug interaction exclusion weighting factor application engine 128. It should be appreciated that these various components of the drug-to-drug interaction system 120 may be provided as software instructions stored in memory and executed by one or more processors of the drug-to-drug interaction system 120, which may be one or more of the processors provided by the server computing device 105, or distributed over a plurality of computing devices, such as server 105 and one or more of the servers 104. Alternatively, some of the logic provided by the components 121-128 may be embodied in hardware devices, firmware, or the like. Moreover, while components 121-128 are shown in FIG. 1 as example components to illustrate the operation of the illustrative embodiments, it should be appreciated that the drug-to-drug interaction system 120 may comprise additional logic that is not specifically shown in FIG. 1 but which may support and assist with the functionality of the components 121-128 shown. Unless otherwise indicated herein, operations or functions described as being performed by the drug-to-drug interaction system 120 that are not specifically attributed to one of the elements 121-128 may be performed by this other logic provided in the drug-to-drug interaction system 120 that is not specifically shown, e.g., controller logic, interface logic, storage logic, and/or the like.

Moreover, while the drug-to-drug interaction system 120 is shown as a separate entity from the cognitive system 100 in FIG. 1 for ease of depiction, it should be appreciated that one or more of the components 121-128 may be integrated in and/or utilize logic and resources of the cognitive system 100 to perform their operations. For example, the drug-to-drug interaction ingestion and machine learning engine 122 may make use of the natural language processing (NLP) and annotator mechanisms of the cognitive system 100 to perform operations for parsing and identifying drug-to-drug interaction information in natural language documents. Moreover, the drug interaction exclusion weighting factor application engine 128 may be integrated with or operate in conjunction with scoring and ranking logic of the cognitive system 100 for scoring and ranking candidate answers, or candidate treatments, in order to select one or more candidate treatments to output as treatment recommendations.

The drug-to-drug interaction ingestion and machine learning engine 122 comprises logic for performing operations to parse and analyze drug-to-drug interaction information in various natural language documents such as drug label information, clinical statements, patient statements, and the like, so as to associate natural language terms/phrases/patterns directed to the interaction of a particular drug of interest in combination with another drug in the drug-to-drug interaction, and to categorize the type of interaction based on one or more of an interaction statement type, medical concepts involved, and possible conditions that may occur as a result of the drug-to-drug interaction. It should be appreciated that these are only example characteristics of a drug-to-drug interaction that may be utilized to categorize a drug-to-drug interaction into an interaction category and other characteristics may be used in other illustrative embodiments in addition to, or in replacement of, one or more of these characteristics without departing from the spirit and scope of the present invention.

It should be appreciated that when parsing and analyzing natural language content of a corpus/corpora 140, many different natural language terms/phrases/patterns may be identified as associated with a particular drug-to-drug interaction. The drug-to-drug interaction ingestion and machine learning engine 122 associates each of the found natural language terms/phrases/patterns in natural language statements describing the drug-to-drug interaction, and categorizes those natural language terms/phrases/patterns with regard to a particular severity category based on a determination of the statement type, possible conditions that may occur from the interaction, and/or medical concepts involved in the interaction. The recognition and identification of drug-to-drug interaction identifiers in natural language, the type of the interaction, possible conditions, and medical concepts may be performed using natural language processing based drug interaction resources 121 that include recognizable terms/phrases and/or natural language patterns which are matched to the natural language terms/phrases/patterns extracted from the statements in the corpus/corpora 140. For example, if a statement is found in the corpus that states "When giving Drug A to a patient taking Drug B, monitor blood pressure of the patient closely as elevation may occur", then the drug-to-drug interaction will be identified from the first portion of the sentence matching a known pattern of key terms/key phrase/pattern, e.g., a pattern of the name of a first drug within 10 words of name of a second drug or a specific pattern of terms, the key natural language phrases that may be extracted by the engine 122 may be to monitor blood pressure and that elevation may occur which are then matched to corresponding patterns/terms/phrases indicative of medical concepts and severity, and thus, an association of the severity category of "monitor" and possible condition of "elevated blood pressure" may occur, with a medical concept of "blood pressure" also being associated with the drug-to-drug interaction.

The drug interaction resources 121 may further comprise information regarding an appropriate delta exclusion score value to be applied to a drug-to-drug interaction based on an association of a particular combination of severity category possible medical conditions resulting from the drug-to-drug interaction, and the medical concepts involved. The "severity" or severity category of a drug-to-drug interaction may be determined from natural language processing of resource documentation and identifying key terms/phrases indicative of various severity categories. In some illustrative embodiments, severity or severity category may be specified as a field or element of a drug interaction resource 121, e.g., the Elsevier Gold Standard database provides a listing of drug interactions along with how severe the interaction is.

As will be described hereafter with reference to the operation of the drug interaction exclusion weighting factor evaluation engine 126, the delta exclusion score values associated with a particular drug-to-drug interaction may be aggregated to generate a total drug interaction exclusion weighting factor for the drug-to-drug interaction. Moreover, the drug interaction resources 121 may comprise other data structures that associate modifications to the delta exclusion score values based on the particular medical concepts involved in a particular drug-to-drug interaction, the possible medical conditions that may result from the drug-to-drug interaction, comorbidity information associated with the particular drug-to-drug interaction, cross referenced patient conditions, and/or other drug-to-drug interaction characteristics that may be specific to a particular drug-to-drug interaction and/or patient. This will be explained in further detail hereafter with regard to FIGS. 3 and 4.

The information in the drug interaction resources 121 may be initially generated prior to operation of the drug-to-drug interaction system 120 and may be provided to the drug-to-drug interaction system 120, such as part of a configuration operation performed prior to operation of the drug-to-drug interaction system 120. However, once configured with the initial content of the drug interaction resources 121, the content may be updated through a machine learning process so as to adjust or modify the information contained therein based on information obtained from future processing of the corpus/corpora 140 and/or user feedback obtained from one or more users, which in many cases will be medical practitioners but may also include patients themselves, health insurance users, governmental organization users, or any other authorized user that may provide such feedback for modifying the content of the drug interaction resources 121 such that the new or updated content will be applied to future evaluations of drug-to-drug interactions when evaluating candidate treatments for patients.

The machine learning performed by the drug-to-drug interaction ingestion and machine learning engine 122 may be performed with regard to the delta exclusion scores of the various combinations of interaction category, possible medical conditions resulting from the drug-to-drug interaction, medical concepts involved, as well as the modification values associated with particular drug-to-drug interaction characteristics and/or patient characteristics, e.g., comorbidities, cross referenced patient attributes or characteristics, medical concepts involved, and the like. For example, an initial set of delta exclusion scores may be associated with each of the combinations for a particular type of natural language pattern, term, phrase, or the like, found in a clinical statement, positional statement, patient statement, or the like, which is defined in the drug interaction resources 121 and recognizable by the drug-to-drug interaction system. A subject matter expert may set these initial delta exclusion scores based on an evaluation of the severity of the drug interaction which may then be modified based on the particular medical concepts involved, e.g., a drug interaction that affects organ functionality may be considered more severe than a drug interaction that affects drowsiness of the patient, and modified based on possible medical conditions that may occur as a consequence of the drug interaction, e.g., a drug interaction that may cause elevated blood pressure may be considered more severe than a drug interaction that causes skin irritation. All of these factors may be combined to generate an initial delta exclusion score for the particular drug interaction based natural language statement pattern, term, or phrase. Through an iterative machine learning process, this initial delta exclusion score may be modified over time as new information is discovered and/or user feedback is received.

It should be appreciated that in some illustrative embodiments, this drug-to-drug interaction based natural language statement pattern may be generic with regard to a plurality of different drug-to-drug interactions. That is, the drug interaction resources 121 may store these drug-to-drug interaction based natural language statement patterns for use in identifying statement patterns, terms, or phrases in natural language content regardless of the particular drugs involved. Thus, for example, a recognizable drug-to-drug interaction based natural language statement pattern may be "monitor blood pressure", with an associated interaction statement type of "monitor", an associated possible condition of "high blood pressure", and an associated medical concept of "blood pressure", with a corresponding delta exclusion score of 0.02. This data structure mapping the drug-to-drug interaction based natural language statement pattern with these drug interaction characteristics and delta exclusion score is drug interaction agnostic and may be applied to natural language content directed to any drug-to-drug interaction.

It should be appreciated that in some cases, the drug-to-drug interaction based natural language statement pattern data structures in the resources 121 may not specify the particular medical concepts involved and may instead specify the recognizable natural language pattern, term, or phrase, the delta exclusion score, the interaction statement type, and the possible conditions arising from a drug interaction of this type, as will be shown in more detail with regard to FIG. 5 hereafter. In such an embodiment, the actual instances of this pattern, term, or phrase with regard to a particular drug-to-drug interaction may be analyzed to identify indicators of medical concepts involved, and those indications may be used to adjust the delta exclusion score to increase or decrease it based on the severity of the medical concepts involved. In this way, the drug interaction resources 121 data structures may be made more applicable to a plurality of different drug-to-drug interactions, and then customized based on the actual references to a particular drug-to-drug interaction based on the medical concepts involved.

For example, for a first interaction that involves Drug A and Drug B, a natural language pattern of "monitor blood pressure" may be associated with the interaction which associates a possible condition of "high blood pressure" and an interaction type category of "monitor" with a corresponding initial delta exclusion score of 0.02. The natural language statement in which this natural language pattern is found may include terms/phrases that reference a medical concept of skin irritation which has a relatively low level of severity and which may reduce the delta exclusion score to 0.01. The same natural language pattern of "monitor blood pressure" may be found in another natural language statement in association with a Drug C and Drug D interaction which again associates the possible condition of "high blood pressure," interaction type category of "monitor," and initial delta exclusion score of 0.02. However, for this interaction, the natural language statement may indicate a medical concept of heart attack or organ failure which is considerably more severe than the skin irritation in the previous example. Thus, based on the medical concept associated with this particular drug-to-drug interaction, the delta exclusion score may be increased to 0.30 or more depending on the particular implementation. Hence, the drug interaction resource data structures may be generically applicable to a plurality of different drug-to-drug interactions and may then be made specific to a particular drug-to-drug interaction based on additional analysis performed by the drug-to-drug interaction ingestion and machine learning engine 122 to identify other medical concepts associated with the natural language patterns, terms, or phrases specified in the drug interaction resources 121 for the particular drug-to-drug interaction found in the natural language content of documents in the corpus/corpora 140.

Over time the delta exclusion scores, or initial delta exclusion scores, specified in the drug interaction resources 121 may be modified based on new information found through analysis or input, e.g., user feedback indicating the correctness/incorrectness of a treatment recommendation based on an exclusion weighting factor applied to a candidate treatment, information found from natural language documentation in the corpus/corpora 140 including, but not limited to, additional possible conditions, medical concepts, or indicators of different levels of severity found in natural language documents, or the like. This may be an automated machine learning process whereby the delta exclusion scores are increased or decreased based on an evaluation of the new information found.

For example, a medical practitioner, presented with treatment recommendations over time that involve a particular drug may provide feedback to the cognitive system 100 indicating the correctness/incorrectness of the cognitive system's evaluation of the appropriateness of the treatment recommendations to the various patients. For a particular drug, the treatment recommendations presented and the feedback gathered may be correlated and used to modify the delta exclusion scores and/or modifiers for various comorbidities, patient attributes, and the like. For example, patients for which a treatment recommendation is made that involve the same drug may have their attributes compared and patients having similar attributes may be grouped. The user feedback for the treatments involving the drug may be analyzed for each group and a modification to the exclusion factor modifiers for the common attributes may be adjusted based on the particular user feedback. For example, assume that treatments involving Drug A have been recommended to a plurality of patients that all have a common attribute of high blood pressure. Based on user feedback from one or more medical practitioners, it may be determined that 75% of the time, recommending a treatment with Drug A is determined by the medical practitioner to be an incorrect recommendation. As a result, the exclusion factor modifier for a patient attribute of "high blood pressure" may be adjusted to increase the exclusion factor modifier so that such treatments may be less often recommended to patients that have high blood pressure. The amount of the increase, or decrease in other examples, may be implementation dependent, e.g., the amount may be calculated based on a relative determination of the level of correctness/incorrectness of the applicability of the drug to particular patient attributes as indicated in user feedback, other drugs taken by patients, comorbidities, or the like. Such machine learning based on user feedback may be performed with regard to a plurality of different elements contributing to the determination of the exclusion factor including, but not limited to, various comorbidities, interaction type categories, medical concepts, cross referenced patient attributes or data, and the like.

Moreover, in addition to, or alternative to, the continuous machine learning described above, in some illustrative embodiments, the machine learning may be trained a priori through the usage of training and validation cases which are comprised of a set of input cases and the "correct" answers for those input cases. These input cases and correct answers are fed into the machine learning mechanisms of the cognitive system 100 and the machine learning adjusts the scoring based on the patterns of scores it sees in the training set.

The drug interaction resources 121 provide a basis by which the corpus/corpora 140 is ingested by the drug-to-drug interaction ingestion and machine learning engine 122 to thereby generate specific drug-to-drug interactions and exclusion factors are generated for drug interactions which are then used to populate data structures in the drug interaction data storage 124. The one or more drug-to-drug interaction data structures in drug interaction data storage 124 represent the particular drug's interaction with one or more other drugs whereas the data structures in the drug interaction resources 121 are of a more generic nature and are applicable to a plurality of drugs, thereby serving as resources for generating the various data structures in the drug interaction data storage 124. The data structure(s) may store, for a drug of interest, a separate data structure for each other drug with which a drug-to-drug interaction has been identified, e.g., for Drug A, there may be separate data structures for each interaction with Drug B, Drug C, Drug D, etc. These separate data structures may comprise an exclusion factor to be applied to the confidence scores or rankings of candidate treatments that involve the drug, e.g., Drug A, when the existence of the other drug in the drug-to-drug interaction is also present with regard to the particular patient, e.g., in the candidate treatment or otherwise being administered to the patient for treatment of the same or another medical condition.

The exclusion factors in the drug interaction data structures of the drug interaction data storage 124 may be calculated by the drug interaction exclusion weighting factor evaluation engine 126 in conjunction with the parsing and analysis performed by the drug-to-drug ingestion and machine learning engine 122, when generating the drug interaction data structures in the storage 124 for particular drugs. In addition, the drug interaction exclusion weighting factor evaluation engine 126 may further utilizes these exclusion factors as base exclusion factors for a drug-to-drug interaction, which may be modified for a particular patient based on additional modifying patient attributes or characteristics for a particular patient to generate a final exclusion factor for the particular drug-to-drug interaction as applied to the particular patient.

The drug interaction exclusion weighting factor application engine 128 receives the candidate treatment information for candidate treatments identified by the cognitive system 100, determines which drug-to-drug interactions apply to the various candidate treatments, and provides the corresponding exclusion factor, or modified exclusion factor for the particular patient, to the cognitive system 100 as an additional factor to include in the scoring and ranking of the candidate treatment. For example, the exclusion factor may be applied to either increase or decrease the score, e.g., confidence score, used for ranking the candidate treatment relative to other candidate treatments. In some embodiments, the exclusion factor may be used to reduce the confidence score of the candidate treatment such that a relatively smaller exclusion factor will indicate less of a reason to exclude the candidate treatment based on drug-to-drug interactions, and a relatively larger exclusion factor will indicate more reason to exclude the candidate treatment based on drug-to-drug interactions, i.e. the candidate treatment is less desirable for the particular patient based on drug-to-drug interactions.

The cognitive system 100 may apply the exclusion factors for the applicable drug-to-drug interactions to the candidate treatments to generate modified confidence scores for the candidate treatments. The candidate treatments may then be ranked based on the modified confidence scores. One or more candidate treatments may be selected based on the ranked candidate treatments as treatment recommendations to be output to a user, e.g., a medical practitioner seeking to treat a patient, the patient themselves, or other authorized personnel. The cognitive system 100 may maintain an association of the exclusion factor information and the particular drug-to-drug interactions associated with these exclusion factors, that affect candidate treatment scoring so as to be able to provide such information in the output of the treatment recommendations to the user. That is, the output may indicate reasons why certain candidate treatments were more or less favorably ranked by specifying that certain candidate treatments were ranked lower because of the drug-to-drug interactions found for the particular candidate treatments, and the severity of such interactions as indicated by the value of the exclusion factor.

The cognitive system 100 may further receive feedback information from users via graphical user interface (GUI) mechanisms presented to users, indicating the correctness/incorrectness of the treatment recommendations in the view of the user. For example, the user may specify for each candidate treatment whether the user believes that the candidate treatment was correctly ranked. This information may then be collected by the cognitive system 100 over a plurality of treatment recommendations, patients, and/or users, and used as part of a machine learning process to modify the delta exclusion scores and/or modifiers to exclusion factors based on a cognitive evaluation of common characteristics of the patients for which the candidate treatments were provided and the corresponding degree of correctness/incorrectness indicated by users.

Thus, the illustrative embodiments provide mechanisms for learning drug-to-drug interactions and determining exclusion factors to be applied to candidate treatments based on these learned drug-to-drug interactions. Moreover, the illustrative embodiments apply the drug-to-drug interactions to the specific attributes of the patient, e.g., comorbidities, cross-referenced patient attributes or data, medical concepts, and the like. The illustrative embodiments may modify the relative scoring and ranking of candidate treatments for the particular patient based on the determined exclusion factors for drug-to-drug interactions associated with the candidate treatments. Furthermore, the illustrative embodiments may output treatment recommendations with information indicating the reasons for the relative rankings of candidate treatments based on drug-to-drug interactions and the severity of such drug-to-drug interactions as indicated by the exclusion factor values. In addition, the illustrative embodiments provide for machine learning based on user feedback, and potentially additional information added to a corpus/corpora, to adjust the delta exclusion scores and/or modifiers to these delta exclusion scores used to generate exclusion factors for drug-to-drug interactions.

Figure 2:
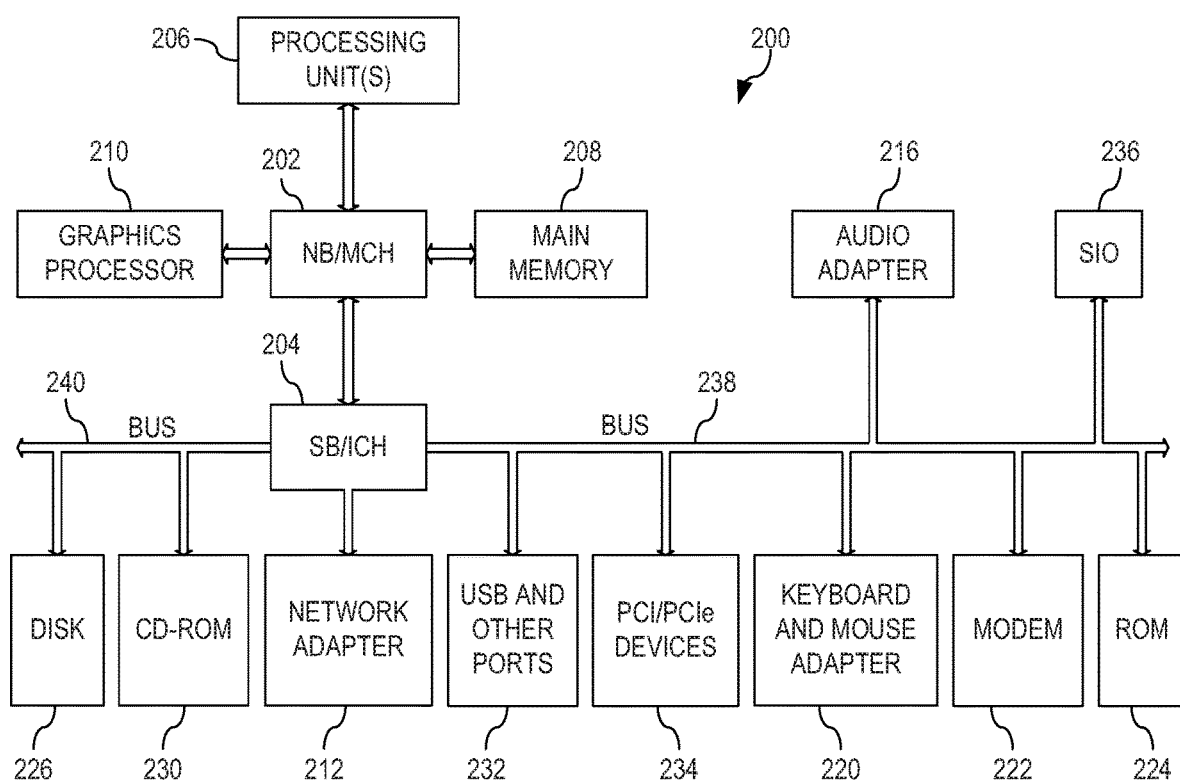
FIG. 2 is a block diagram of an example data processing system in which aspects of the illustrative embodiments are implemented.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
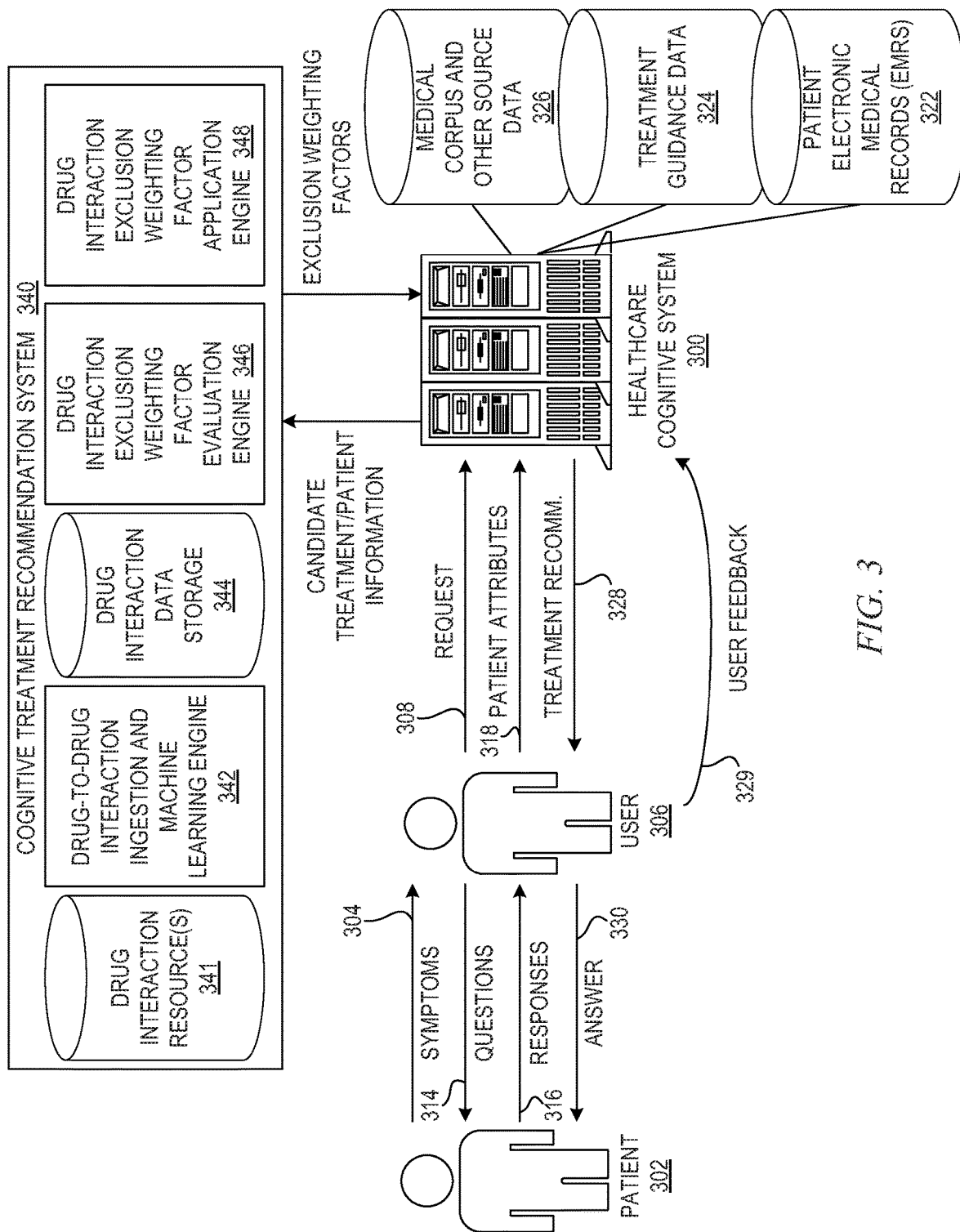
FIG. 3 is an example diagram illustrating an interaction of elements of a healthcare cognitive system in accordance with one illustrative embodiment.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare cognitive operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical condition to a user 306, such as a healthcare practitioner, technician, or the like. The user 306 may interact with the patient 302 via a question 314 and response 316 exchange where the user gathers more information about the patient 302, the symptoms 304, and the medical condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318, the medical condition diagnosed by the user 306, or the like. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304, medical condition, and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

One example of a healthcare cognitive system 300 which may be implemented and modified to incorporate the operations of the cognitive treatment recommendation system 340 of one or more of the illustrative embodiments, is described in co-pending and commonly assigned U.S. patent application Ser. No. 15/262,311, filed Sep. 12, 2016 and entitled "Medical Condition Independent Engine for Medical Treatment Recommendation System," which is hereby incorporated by reference. It should be appreciated that this is only one example of a cognitive healthcare system with which the mechanisms of the illustrative embodiments may be utilized. The mechanisms of the illustrative embodiments may be implemented with any cognitive healthcare system that evaluates patient EMR data and candidate treatment data to generate a treatment recommendation for treating the patient.

In accordance with the illustrative embodiments herein, the healthcare cognitive system 300 is augmented to include, or operate in conjunction with, the cognitive treatment recommendation system 340 which operates in the manner described previously, with regard to the similar system 120 in FIG. 1 and one or more of the illustrative embodiments described above. The depiction in FIG. 3 is showing runtime operation of the cognitive treatment recommendation system 340 for assisting with the evaluation of candidate treatments for a particular patient. As such, it is assumed that the drug-to-drug interaction ingestion and machine learning engine 342 has already performed its initial operations for ingesting a corpus/corpora of information to generate data structures in the drug interaction data storage 344 based on the drug interaction resources 341, such as previously described above.

During runtime operation, the healthcare cognitive system 300 generates candidate treatments for the patient and provides this information along with patient information, e.g., patient EMR and demographic information, to the cognitive treatment recommendation system 340. The cognitive treatment recommendation system 340 analyzes the candidate treatments to identify the drugs involved in the candidate treatments, identifies the drugs indicated as being actively administered to the patient for the same or different medical condition for which the candidate treatments are being considered, to thereby identify the drugs being taken by the patient and the drugs that are potentially going to be administered to the patient should the various candidate treatments be selected for treating the patient. The drug-to-drug interactions associated with pairings of the identified drugs may be retrieved from the drug interaction data storage 344 and corresponding exclusion factors may be provided to the drug interaction exclusion weighting factor evaluation engine 346.

The drug interaction exclusion weighting factor evaluation engine 346 may evaluate the particular patient attributes as specified in the patient EMR and demographic information provided by the healthcare cognitive system 300 to apply additional modifications to the exclusion weighting factor, also referred to herein as an exclusion factor, based on the particular patient to thereby tailor the exclusion factor to the particular health situation of the particular patient. The drug interaction exclusion weighting factor application engine 348 then applies these exclusion weighting factors to the corresponding candidate treatments to which they are applicable and provides those exclusion weighting factors back to the healthcare cognitive system 300 which then applies these exclusion weighting factors to the confidence score calculation and ranking of the candidate treatments generated by the healthcare cognitive system 300. The healthcare cognitive system 300 then selects one or more of these candidate treatments to return to the user 306 as a treatment recommendation 328.

As mentioned previously, in some illustrative embodiments, this treatment recommendation 328 may include a ranked listing of candidate treatments with corresponding explanations as to why certain candidate treatments are ranked lower based on drug-to-drug interactions. These explanations may indicate the specific drugs in the drug-to-drug interactions that are causing a reduction in the ranking of the candidate treatment, as well as a severity of the drug-to-drug interaction as indicated by the exclusion factor applied to the candidate treatment. The output of the treatment recommendation 328 may comprise a graphical user interface through which the user 306 may provide user feedback indicating the user's view as to the correctness/incorrectness of the candidate treatment ranking and/or recommended treatments. This user feedback 329 may be provided back to the healthcare cognitive system 300 and may be used to modify, through machine learning, such as provided by engine 342, the delta exclusion scores and/or modifiers applied to these delta exclusion scores and/or exclusion factors, as previously discussed above. It should also be appreciated that when there are modifications to the content of the corpus/corpora 140, or 322-326, or at periodic times, the corpus/corpora 140 may be re-evaluated to update or modify, through machine learning, these delta exclusion scores and/or exclusion factors and modifiers to such scores/factors.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention. It should be appreciated, however, that at no time should the treatment itself be administered to the patient 302 without prior approval of the healthcare professional treating the patient, i.e. final determinations as to treatments given to a patient will always fall on the healthcare professional with the mechanisms of the illustrative embodiments serving only as an advisory tool for the healthcare professional (user 306) and/or patient 302.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P."

Figure 4:
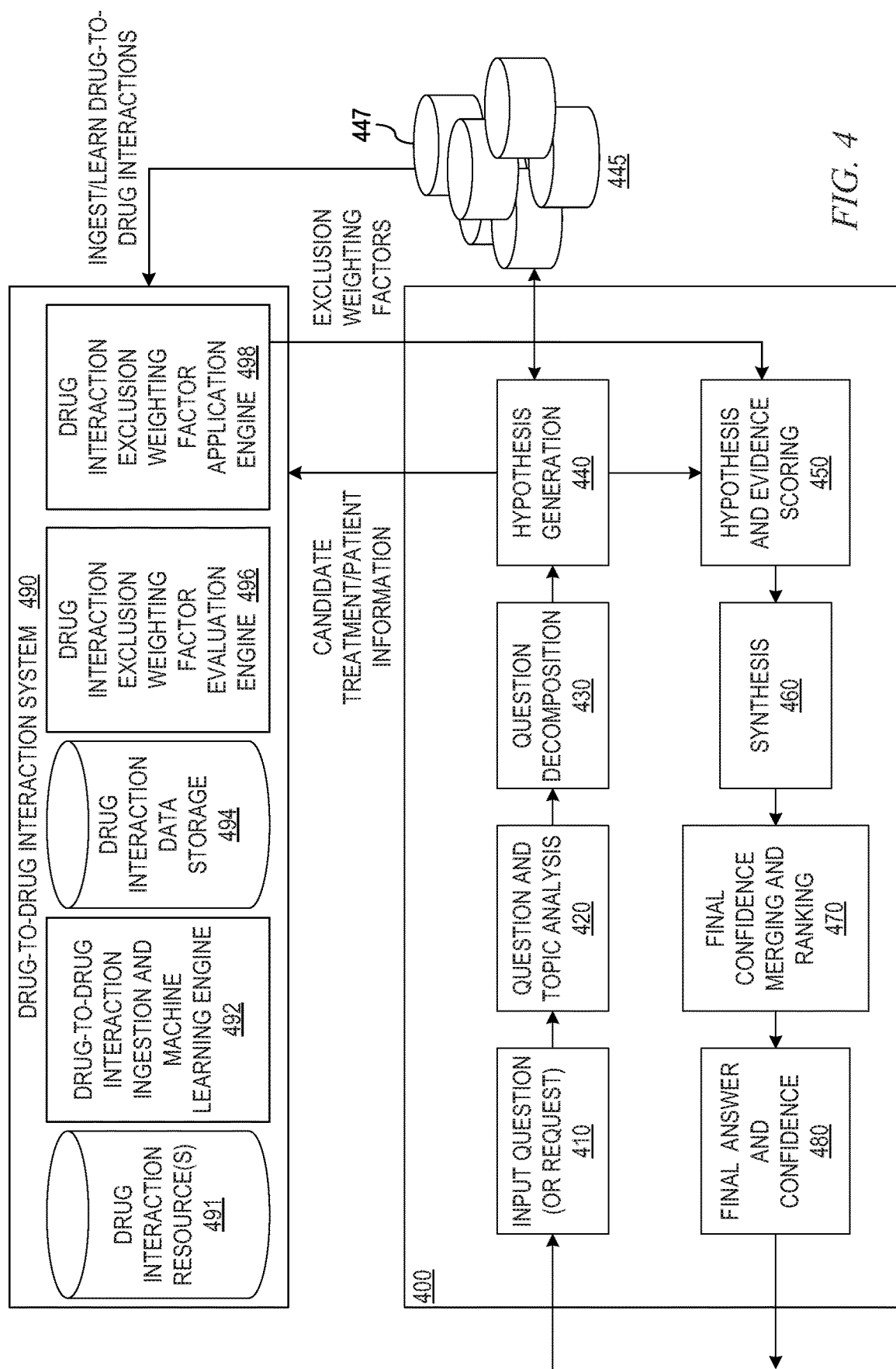
FIG. 4 illustrates a cognitive healthcare system implementing a Question and Answer (QA) or request processing pipeline for processing an input question or request in accordance with one illustrative embodiment.

FIG. 4 illustrates a QA pipeline of a healthcare cognitive system, such as healthcare cognitive system 300 in FIG. 3, or an implementation of cognitive system 100 in FIG. 1, for processing an input question in accordance with one illustrative embodiment. It should be appreciated that the stages of the QA pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

As shown in FIG. 4, the QA pipeline 400 comprises a plurality of stages 410-480 through which the cognitive system operates to analyze an input question and generate a final response. In an initial question input stage 410, the QA pipeline 400 receives an input question that is presented in a natural language format. That is, a user inputs, via a user interface, an input question for which the user wishes to obtain an answer, e.g., "What medical treatments for diabetes are applicable to a 60 year old patient with cardiac disease?" In response to receiving the input question, the next stage of the QA pipeline 400, i.e. the question and topic analysis stage 420, parses the input question using natural language processing (NLP) techniques to extract major features from the input question, and classify the major features according to types, e.g., names, dates, or any of a plethora of other defined topics. For example, in a question of the type "Who were Washington's closest advisors?", the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases, classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 4, the identified major features are then used during the question decomposition stage 430 to decompose the question into one or more queries that are applied to the corpora of data/information 445 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 445. That is, these various sources themselves, different collections of sources, and the like, represent a different corpus 447 within the corpora 445. There may be different corpora 447 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 447 within the corpora 445.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 440, to generate hypotheses for answering the input question. These hypotheses are also referred to herein as "candidate answers" for the input question. For any input question, at this stage 440, there may be hundreds of hypotheses or candidate answers generated that may need to be evaluated.

The QA pipeline 400, in stage 450, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 460, the large number of scores generated by the various reasoning algorithms are synthesized into confidence scores or confidence measures for the various hypotheses. This process involves applying weights to the various scores, where the weights have been determined through training of the statistical model employed by the QA pipeline 400 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 400 that identifies a manner by which these scores may be combined to generate a confidence score or measure for the individual hypotheses or candidate answers. This confidence score or measure summarizes the level of confidence that the QA pipeline 400 has about the evidence that the candidate answer is inferred by the input question, i.e. that the candidate answer is the correct answer for the input question.

The resulting confidence scores or measures are processed by a final confidence merging and ranking stage 470 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 480, a final answer and confidence score, or final set of candidate answers and confidence scores, are generated and output to the submitter of the original input question via a graphical user interface or other mechanism for outputting information.

As shown in FIG. 4, in accordance with one illustrative embodiment, the drug-to-drug (D2D) interaction system 490 ingests and learns drug interactions, during an initial ingestion operation for ingesting portions of the corpora 445, and identifies applicable initial delta exclusion scores and calculates specific exclusion factors for particular drug-to-drug interactions using the mechanisms 491-493, which operate similar to that described above with regard to similar elements shown in FIGS. 1 and 3. In addition, the D2D interaction system 490 may be informed of various factors applying to D2D interactions including comorbidities, particular cross referenced patient attributes that affect the level of exclusion of the drugs in the D2D interactions, and the like, from the corpus/corpora 445, 447. This learned drug interaction information, as represented in the data structures of the drug interaction data storage 494, may be applied to a particular set of candidate treatments and patient information provided by the hypothesis generation stage logic 440 of the QA system pipeline 400.

The drug interaction exclusion weighting factor evaluation engine 496 and drug interaction exclusion factor application engine 498 operate to identify the D2D interactions and their corresponding exclusion factors that apply to the candidate treatments, modify those exclusion factors based on patient information, and generate final exclusion factors for the various candidate treatments which are then provided back to the hypothesis and evidence scoring stage logic 450 of the QA system pipeline 400. These final exclusion factors are used to modify the confidence scoring and thus, the relative ranking, of the candidate treatments. Thereafter, the stages 46-480 may operate as previously discussed above with the exception that the final answer and confidence 480 may generate an output that includes a GUI with explanations as to the D2D interactions and their severity with regard to the various candidate treatments, and providing user interface elements which may be used to provide user feedback.

It should be appreciated that as part of the ingestion operation for ingesting the corpus/corpora 445, 447, along with the natural language processing previously described above, with regard to D2D interactions, the natural language processing performed on this corpus/corpora 445, 447 may operate to identify and extract key features, such as, for example, terms/phrases and numerical values/ranges, indicative of drug-to-drug interactions including the names or other identifiers of the drugs involved, the severity of such interactions between these drugs, the medical concepts associated with the interactions, the requirements for administering multiple drugs as part of a same or different treatment, patient attributes that may influence the drug-to-drug interactions, and the possible conditions that may arise as a result of the drug-to-drug interactions. The drug-to-drug interaction information may be provided in a structured or non-structured manner in the natural language documentation of the corpus/corpora. In many cases, this drug-to-drug interaction will be provided as one or more natural language statements in the structured or non-structured portions of the natural language documentation. The natural language processing may be performed, at least in part, by one or more annotators of the QA system and/or QA system pipeline 400 that are specifically configured to identify terms, phrases, numerical values and/or ranges, and other indicators of key features of drug-to-drug interaction information, including, but not limited to, severity of the interaction, comorbidity statements, category type of the interaction, and various other medical concepts specified in natural language, such as clinical statements and patient statements.

In determining the severity of the terms/phrases, the algorithms or annotators may perform various methods of evaluation of the terms/phrases in the context of the particular effects of the drug interaction, the possible resulting effects, the relative importance of the medical concepts to the overall health of the patient (e.g., side effects associated with the patient's vital organs are more important than side effects directed to comfort of the patient, such as rashes, headaches, etc.), other uses of similar terms/phrases of severity in other drug interactions, and the like. For example, if the term/phrase is "avoid", this term can be interpreted with various levels of severity. In the context of a drug interaction that affects a patient's mental acuity, and where the possible resulting conditions may include heart problems the term "avoid" can be considered to represent a relatively high severity. In the context of a drug interaction that results in a headache, the term "avoid" may be considered relatively low in severity.

Various weight values may be associated with the features of the drug interaction information extracted by the natural language processing. These weight values may be combined to arrive at an exclusion factor to be applied to the particular D2D interaction for treatment recommendations. Again, this exclusion factor may be considered a baseline exclusion factor for the D2D interaction which may be further modified based on the particular patient attributes. Thus, for example, the severity of the interaction, the comorbidity statement factors, the category type of the interaction, and other involved medical concepts may each have a numerical representation indicative of their relative importance or severity in the determination of whether the particular candidate treatment should be excluded.

One example of a formula that may be used to calculate an exclusion factor is as follows:

Severity+CM Statements+Category Type+Medical Concepts=Exclusion Factor

A mapping for the severity level or category for each statement will be defined for each of the items above. Thus for example, the severity may be provided as a three level mapping with corresponding delta exclusion score ranges associated with these levels. The particular delta exclusion score to be applied from within each range may be determined based on other modifying factors found in the natural language statements, e.g., sentiment analysis mechanisms, numbers of occurrences of mentions of such D2D interactions in the corpus/corpora, and the like. The following is an example embodiment of a three level mapping of severity to delta exclusion score based on a 0.0 to 1.0 scale:

Severity 1—is an absolute exclusion that carries an exclusion factor of 0.5-1.0 depending on other elements found in the corpus/corpora.

Severity 2—0.25 to 0.49 depending on the elements found in the corpus/corpora.

Severity 3—0.01 to 0.24 depending on other elements found in the corpus/corpora.

Other factors for medical concepts can further add to the exclusion factor, e.g., a primary organ being affected by the D2D interaction may add between 0.1 and 0.3 to the final exclusion factor. For example, the following is one example of the calculation of a final exclusion factor that may be generated for a particular patient based on the baseline exclusion factor calculated for the D2D interaction, the comorbidities (CMs) associated with the medical condition being treated, and the cross-referenced patient attributes.

Baseline Exclusion Score (indicative of Severity of D2D interaction) (0.25)+CM Monitor (0.02)+CM Monitor (0.02)+CM Monitor renal (0.04)+Category Type (Monitor)+(0.02)+Medical Concept (Renal=Kidney) 0.02+Cross Referenced Patient Data for Kidney Health (Great Health 0.04 or Good Health 0.1+Some Issues Health 0.25, Major Issues Health 0.5)=Exclusion Score (0.25+0.02+0.02+0.02+0.04+0.02+0.25 Some Health Issues)=0.62 Exclusion Factor The resulting exclusion factor for the particular patient may be used, as discussed above, during treatment recommendation to assist in ranking candidate treatment recommendations based on any determination of possible drug-to-drug interactions involved in the treatment recommendations such that those having relatively larger exclusion factors are ranked lower than those that have relatively smaller exclusion factors.

FIG. 5 is an example diagram of a data structure of a drug interaction resource in accordance with one illustrative embodiment. The D2D interaction resource data structure 500 in FIG. 5 may be provided in the drug interaction resources 121, 341, or 491, for example, and may be used to provide the delta exclusion scores for application to particular D2D interaction instances found in natural language content of a corpus or corpora in order to generate D2D interaction specific exclusion factors, which may then be modified for particular patients when evaluating candidate treatments for particular patients.

As shown in FIG. 5, the D2D interaction resource data structure 500 includes a first column for statement patterns that includes terms/phrases/natural language patterns that are indicative of a D2D interaction between multiple drugs. A second column is provided that includes the initial delta exclusion score for D2D interactions that are found in natural language content where the natural language content referencing the D2D interactions have terms/phrases/natural language patterns that match the corresponding terms/ phrases/natural language pattern in the first column. A third column includes information about the statement type which may be indicative of the severity of the statement that matches the statement pattern of the first column. The fourth column specifies conditions that may result from a D2D interaction referenced in a statement matching the statement pattern of the first column.

As noted above, when generating an exclusion factor, or baseline exclusion factor, for a particular D2D interaction, the natural language statement in the corpus/corpora referencing the D2D interaction may have terms/phrases/natural language patterns that match the statement pattern in the resource data structure 500. The corresponding delta exclusion score, statement type, and conditions may be retrieved and together used to generate a baseline exclusion score. In addition, information regarding comorbidities, cross-referenced patient attributes, and the like may also be identified and used to add to the baseline exclusion score calculation. The resulting baseline exclusion score may be stored in a specific D2D interaction data structure as discussed above, that is specific to the particular pairing of drugs, e.g., Drug A with Drug B. It should be appreciated that the statement patterns in data structure 500 are generic and not specific to any particular drug or D2D interaction. Moreover, statements directed to a specific D2D interaction in the corpus/corpora may comprise terms/phrases/or natural language patterns that match more than one of the statement patterns in data structure 500 and all applicable matches would be returned and used to generate a baseline exclusion factor for the specific D2D interaction.

Figure 6:
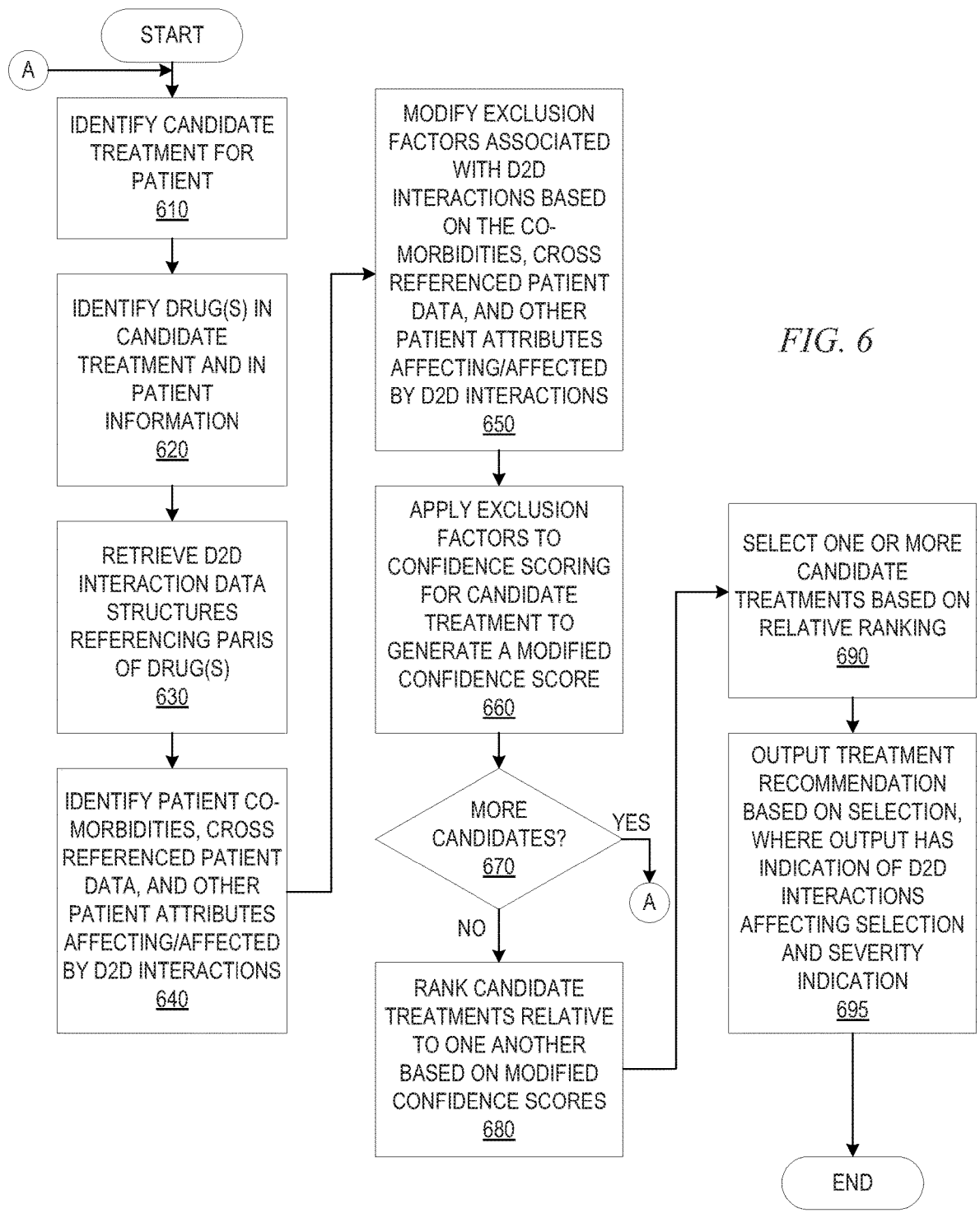
FIG. 6 is a flowchart outlining an operation for generating a treatment recommendation taking into consideration drug-to-drug (D2D) interactions in accordance with one illustrative embodiment.

FIG. 6 is a flowchart outlining an example operation for generating a drug-to-drug (D2D) interaction exclusion factor and applying it to a confidence score and ranking of a candidate treatment in accordance with one illustrative embodiment. The operation in FIG. 6 assumes that the D2D interaction engine has already been configured with D2D interaction resource data structures, and has ingested a corpus/corpora of electronic documentation that includes D2D interaction information, to thereby generate specific D2D interaction data structures that may be applied to candidate treatments. The operation outlined in FIG. 6 may be implemented by the D2D interaction system in response to a cognitive system providing candidate treatment and patient information to the D2D interaction system for evaluation, for example.

As shown in FIG. 6, the operation starts by identifying a candidate treatment for a patient (step 610). The identifying may be done by a cognitive healthcare system such as previously described above which processes a request for a treatment recommendation, such as through a request or question processing pipeline, evaluates a corpus/corpora of information including patient EMRs, medical knowledge documentation, and the like, to generate one or more candidate treatments for the medical condition of the patient. The drugs in the candidate treatment and supplied patient information are identified (step 620) and corresponding D2D interaction data structures that reference pairings of these identified drugs are retrieved from the D2D interaction data storage (step 630). It should be appreciated that the data structures in the D2D interaction data storage may have been previously generated based on the D2D interaction resources, natural language statements found in the corpus/corpora that reference the specific D2D interaction and which match patterns specified in the D2D interaction resources, evaluation of the corresponding delta exclusion scores, medical concepts associated with the D2D interaction referenced in natural language statements, and the like, as previously described above.

The operation then identifies, for the particular patient and the patient information provided by the cognitive healthcare system, the patient co-morbidities, cross-reference patient data or attributes, and other patient attributes that affect or are affected by the D2D interactions (step 640). The exclusion factors associated with the D2D interactions, as identified in the retrieved D2D interaction data structures, are modified based on these patient co-morbidities, cross-referenced patient data or attributes, and other patient attributes (step 650). The exclusion factors that are generated in this manner are then applied to the confidence scoring for the candidate treatment to generate a modified confidence score (step 660).

A determination is made as to whether there are more candidate treatments to be evaluated with regard to D2D interactions (step 670). If so, the operation returns to step 610 and the operation is repeated for a next candidate treatment (step 680). If there are no further candidate treatments to process, then a ranking of the candidate treatments relative to one another based on the modified confidence scores is generated (step 680). One or more candidate treatments are selected from the relative ranking (step 690) and an output is generated that outputs a treatment recommendation to a user based on the selection (step 695). The output may be in the form of a graphical user interface that includes information as to the found D2D interactions and their relative severity which affected the selection of the treatment recommendation. Moreover, the GUI may include GUI elements for receiving user feedback as to the user's view on the correctness/incorrectness of the treatment recommendation and scoring of candidate treatments based on D2D interactions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a cognitive medical treatment recommendation system, the method comprising:
   executing a drug-to-drug interaction ingestion and machine learning engine that performs an automated machine learning operation on a current set of delta exclusion values, corresponding to a plurality of different combinations of drug-to-drug interaction natural language statement patterns in natural language content, and one or more drug interaction factors corresponding to the drug-to-drug interaction natural language statement patterns, to generate a modified set of delta exclusion values and update the current set of delta exclusion values based on the modified set of delta exclusion values;
   storing, in a drug interaction resource data storage, for each of the different combinations of drug-to-drug interaction natural language statement patterns, a corresponding delta exclusion value from the current set of delta exclusion values in association with the drug-to-drug interaction natural language statement pattern;
   ingesting, by the cognitive medical treatment recommendation system, a corpus of medical treatment content, wherein the medical treatment content comprises drug-to-drug interaction information specified in natural language of the corpus of medical treatment content;
   generating, by the cognitive medical treatment recommendation system, a set of drug interaction insight data structures based on the ingested corpus of medical treatment content at least by performing computer executed natural language processing of the natural language of the corpus of medical treatment content to extract natural language elements corresponding to drug-to-drug interactions and generate the set of drug interaction insight data structures based on the extracted natural language elements;
   generating, by the cognitive medical treatment recommendation system, an initial set of candidate treatments for a medical condition of a patient based on an analysis of one or more electronic medical records (EMRs) associated with the patient;
   ranking, by the cognitive medical treatment recommendation system, candidate treatments in the initial set of candidate treatments based on the set of drug interaction insight data structures to generate a final set of candidate treatments, wherein the ranking reduces at least one ranking of a candidate treatment, in which a drug interaction is identified in a corresponding drug interaction insight data structure of the set of drug interaction insight data structures, by an amount of an exclusion weighting factor specified in the corresponding drug interaction insight data structure; and
   outputting, by the cognitive medical treatment recommendation system, a treatment recommendation based on the final set of candidate treatments, wherein generating the set of drug interaction insight data structures comprises:
      analyzing, by the cognitive medical treatment recommendation system, the drug-to-drug interaction information to categorize each drug-to-drug interaction referenced in the corpus of medical treatment content, into a severity category based on a measure of severity of the drug-to-drug interaction; and
      calculating, for each drug interaction insight data structure, a corresponding exclusion weighting factor based on a severity category of the drug-to-drug interaction associated with the drug interaction insight data structure, and delta exclusion values corresponding to drug-to-drug interaction natural language statement patterns present in the extracted natural language elements that correspond to the drug interaction insight data structure.

2. The method of claim 1, wherein ranking the candidate treatments in the initial set of candidate treatments to generate a final set of candidate treatments comprises applying, to candidate treatments comprising a drug having a drug-to-drug interaction specified in a drug interaction insight data structure with another drug being taken by the patient, the corresponding exclusion weighting factor to a confidence score associated with the candidate treatment.

3. The method of claim 1, wherein the corpus of medical treatment content comprises natural language electronic documents comprising at least one of drug label documents comprising drug-to-drug interaction information, clinical statement documents comprising clinical statements from medical personnel describing drug-to-drug interactions, or patient statement documents comprising patient statements from patients describing drug-to-drug interactions.

4. The method of claim 1, wherein each drug interaction insight data structure specifies at least two drugs for which a negative result is determined to occur if the at least two drugs are administered to a patient, and the corresponding exclusion weighting value applicable to scores generated for candidate treatments that include at least one of the at least two drugs, in response to a determination that the patient is also prescribed another of the at least two drugs.

5. The method of claim 4, wherein ranking the candidate treatments in the initial set of candidate treatments based on the set of drug interaction insight data structures to generate a final set of candidate treatments, comprises, for each candidate treatment, and for each drug interaction insight data structure corresponding to a drug prescribed to the patient:

determining whether the EMRs associated with the patient indicate that the patient has been prescribed another drug in the at least two drugs of the drug interaction insight data structure; and applying the corresponding exclusion weighting factor associated with the drug interaction insight data structure to a score associated with the candidate treatment in response to a determination that the EMRs indicate that the patient has been prescribed another of the at least two drugs.

6. The method of claim 1, wherein ranking the candidate treatments in the initial set of candidate treatments based on the set of drug interaction insight data structures to generate a final set of candidate treatments comprises, for each candidate treatment in the initial set of candidate treatments:

identifying at least one drug that is part of the candidate treatment;

identifying, for the at least one drug, at least one drug interaction data structure associated with the at least one drug;

identifying, for each drug interaction data structure in the at least one drug interaction data structure, a delta exclusion factor specified in the associated drug interaction data structure;

determining, for each drug interaction data structure associated with the drug, whether a drug interaction represented by the drug interaction data structure applies to the patient based on the EMRs associated with the patient and criteria specified in the drug interaction data structure; and accumulating the delta exclusion factors for each drug interaction, represented by each of the drug interaction data structures, that apply to the patient to generate an exclusion weighting factor for the candidate treatment that is applied to a score for the candidate treatment.

7. The method of claim 6, wherein determining whether the drug interaction applies to the patient based on the EMRs associated with the patient comprises modifying the delta exclusion factor associated with a drug interaction associated with the drug, based on a matching of portions of the EMRs associated with the patient to criteria of the drug interaction specified in the drug interaction data structure.

8. The method of claim 1, wherein storing for each of the different combinations of drug-to-drug interaction natural language statement patterns, a corresponding delta exclusion value further comprises storing, in association with the drug-to-drug interaction natural language statement pattern, a possible medical condition associated with the drug-to-drug interaction natural language statement pattern and an interaction statement type specifying an interaction to be performed with regard to the medical condition.

9. The method of claim 1, wherein the cognitive medical treatment recommendation system comprises one or more machine learning trained question answering pipelines operating on one or more corresponding corpora to generate treatment recommendations based on evidence data present in the one or more corresponding corpora.

10. A computer program product comprising a computer readable storage medium having a computer readable program stored therein, wherein the computer readable program, when executed on a computing device, causes the computing device to implement a cognitive medical treatment recommendation system which operates to:

execute a drug-to-drug interaction ingestion and machine learning engine that performs an automated machine learning operation on a current set of delta exclusion values, corresponding to a plurality of different combinations of drug-to-drug interaction natural language statement patterns in natural language content, and one or more drug interaction factors corresponding to the drug-to-drug interaction natural language statement patterns, to generate a modified set of delta exclusion values and update the current set of delta exclusion values based on the modified set of delta exclusion values;

store, in a drug interaction resource data storage, for each of the different combinations of drug-to-drug interaction natural language statement patterns, a corresponding delta exclusion value from the current set of delta exclusion values in association with the drug-to-drug interaction natural language statement pattern;

ingest a corpus of medical treatment content, wherein the medical treatment content comprises drug-to-drug interaction information specified in natural language of the corpus of medical treatment content;

generate a set of drug interaction insight data structures based on the ingested corpus of medical treatment content at least by performing computer executed natural language processing of the natural language of the corpus of medical treatment content to extract natural language elements corresponding to drug-to-drug interactions and generate the set of drug interaction insight data structures based on the extracted natural language elements;

generate an initial set of candidate treatments for a medical condition of a patient based on an analysis of one or more electronic medical records (EMRs) associated with the patient;

rank candidate treatments in the initial set of candidate treatments based on the set of drug interaction insight data structures to generate a final set of candidate treatments, wherein the ranking reduces at least one ranking of a candidate treatment, in which a drug interaction is identified in a corresponding drug interaction insight data structure of the set of drug interaction insight data structures, by an amount of an exclusion weighting factor specified in the corresponding drug interaction insight data structure; and output a treatment recommendation based on the final set of candidate treatments, wherein the computer readable program further causes the cognitive medical treatment recommendation system to generate the set of drug interaction insight data structures at least by:

analyzing, by the cognitive medical treatment recommendation system, the drug-to-drug interaction information to categorize each drug-to-drug interaction, referenced in the corpus of medical treatment content, into a severity category based on a measure of severity of the drug-to-drug interaction; and calculating, for each drug interaction insight data structure, a corresponding exclusion weighting factor based on a severity category of the drug-to-drug interaction associated with the drug interaction insight data structure, and delta exclusion values corresponding to drug-to-drug interaction natural language statement patterns present in the extracted natural language elements that correspond to the drug interaction insight data structure.

11. The computer program product of claim 10, wherein the computer readable program further causes the cognitive medical treatment recommendation system to rank the candidate treatments in the initial set of candidate treatments to generate a final set of candidate treatments at least by applying, to candidate treatments comprising a drug having a drug-to-drug interaction specified in a drug interaction insight data structure with another drug being taken by the patient, the corresponding exclusion weighting factor to a confidence score associated with the candidate treatment.

12. The computer program product of claim 10, wherein the corpus of medical treatment content comprises natural language electronic documents comprising at least one of drug label documents comprising drug-to-drug interaction information, clinical statement documents comprising clinical statements from medical personnel describing drug-to-drug interactions, or patient statement documents comprising patient statements from patients describing drug-to-drug interactions.

13. The computer program product of claim 10, wherein each drug interaction insight data structure specifies at least two drugs for which a negative result is determined to occur if the at least two drugs are administered to a patient, and the corresponding exclusion weighting value applicable to scores generated for candidate treatments that include at least one of the at least two drugs, in response to a determination that the patient is also prescribed another of the at least two drugs.

14. The computer program product of claim 13, wherein the computer readable program further causes the cognitive medical treatment recommendation system to rank the candidate treatments in the initial set of candidate treatments based on the set of drug interaction insight data structures to generate a final set of candidate treatments, at least by, for each candidate treatment, and for each drug interaction insight data structure corresponding to a drug prescribed to the patient:
 determining whether the EMRs associated with the patient indicate that the patient has been prescribed another drug in the at least two drugs of the drug interaction insight data structure; and
 applying the corresponding exclusion weighting factor associated with the drug interaction insight data structure to a score associated with the candidate treatment in response to a determination that the EMRs indicate that the patient has been prescribed another of the at least two drugs.

15. The computer program product of claim 10, wherein the computer readable program further causes the cognitive medical treatment recommendation system to rank the candidate treatments in the initial set of candidate treatments based on the set of drug interaction insight data structures to generate a final set of candidate treatments at least by, for each candidate treatment in the initial set of candidate treatments:
 identifying at least one drug that is part of the candidate treatment;
 identifying, for the at least one drug, at least one drug interaction data structure associated with the at least one drug;
 identifying, for each drug interaction data structure in the at least one drug interaction data structure, a delta exclusion factor specified in the associated drug interaction data structure;
 determining, for each drug interaction data structure associated with the drug, whether a drug interaction represented by the drug interaction data structure applies to the patient based on the EMRs associated with the patient and criteria specified in the drug interaction data structure; and
 accumulating the delta exclusion factors for each drug interaction, represented by each of the drug interaction data structures, that apply to the patient to generate an exclusion weighting factor for the candidate treatment that is applied to a score for the candidate treatment.

16. The computer program product of claim 15, wherein the computer readable program further causes the cognitive medical treatment recommendation system to determine whether the drug interaction applies to the patient based on the EMRs associated with the patient at least by modifying the delta exclusion factor associated with a drug interaction associated with the drug, based on a matching of portions of the EMRs associated with the patient to criteria of the drug interaction specified in the drug interaction data structure.

17. The computer program product of claim 10, wherein storing for each of the different combinations of drug-to-drug interaction natural language statement patterns, a corresponding delta exclusion value further comprises storing, in association with the drug-to-drug interaction natural language statement pattern, a possible medical condition associated with the drug-to-drug interaction natural language statement pattern and an interaction statement type specifying an interaction to be performed with regard to the medical condition.

18. An apparatus comprising:
 at least one processor; and
 at least one memory coupled to the at least one processor, wherein the at least one memory comprises instructions which, when executed by the at least one processor, cause the at least one processor to:
 execute a drug-to-drug interaction ingestion and machine learning engine that performs an automated machine learning operation on a current set of delta exclusion values, corresponding to a plurality of different combinations of drug-to-drug interaction natural language statement patterns in natural language content, and one or more drug interaction factors corresponding to the drug-to-drug interaction natural language statement patterns, to generate a modified set of delta exclusion values and update the current set of delta exclusion values based on the modified set of delta exclusion values;
 store, in a drug interaction resource data storage, for each of the different combinations of drug-to-drug interaction natural language statement patterns, a corresponding delta exclusion value from the current set of delta exclusion values in association with the drug-to-drug interaction natural language statement pattern;
 ingest a corpus of medical treatment content, wherein the medical treatment content comprises drug-to-drug interaction information specified in natural language of the corpus of medical treatment content;
 generate a set of drug interaction insight data structures based on the ingested corpus of medical treatment content at least by performing computer executed natural language processing of the natural language of the corpus of medical treatment content to extract natural language elements corresponding to drug-to-drug interactions and generate the set of drug interaction insight data structures based on the extracted natural language elements;

generate an initial set of candidate treatments for a medical condition of a patient based on an analysis of one or more electronic medical records (EMRs) associated with the patient;

rank candidate treatments in the initial set of candidate treatments based on the set of drug interaction insight data structures to generate a final set of candidate treatments, wherein the ranking reduces at least one ranking of a candidate treatment, in which a drug interaction is identified in a corresponding drug interaction insight data structure of the set of drug interaction insight data structures, by an amount of an exclusion weighting factor specified in the corresponding drug interaction insight data structure; and output a treatment recommendation based on the final set of candidate treatments, wherein the computer readable program further causes the cognitive medical treatment recommendation system to generate the set of drug interaction insight data structures at least by:

analyzing, by the cognitive medical treatment recommendation system, the drug-to-drug interaction information to categorize each drug-to-drug interaction, referenced in the corpus of medical treatment content, into a severity category based on a measure of severity of the drug-to-drug interaction; and calculating, for each drug interaction insight data structure, a corresponding exclusion weighting factor based on a severity category of the drug-to-drug interaction associated with the drug interaction insight data structure, and delta exclusion values corresponding to drug-to-drug interaction natural language statement patterns present in the extracted natural language elements that correspond to the drug interaction insight data structure.

19. The apparatus of claim 18, wherein storing for each of the different combinations of drug-to-drug interaction natural language statement patterns, a corresponding delta exclusion value further comprises storing, in association with the drug-to-drug interaction natural language statement pattern, a possible medical condition associated with the drug-to-drug interaction natural language statement pattern and an interaction statement type specifying an interaction to be performed with regard to the medical condition.

20. The apparatus of claim 18, wherein the cognitive medical treatment recommendation system comprises one or more machine learning trained question answering pipelines operating on one or more corresponding corpora to generate treatment recommendations based on evidence data present in the one or more corresponding corpora.

* * * * *